United States Patent [19]

Umekawa et al.

[11] Patent Number: 4,518,610
[45] Date of Patent: May 21, 1985

[54] MICROBICIDAL/MICROBISTATIC COMPOSITIONS AND USE THEREOF EMPLOYING MIXTURES OF 4,5-DICHLORO-1,2-DITHIOL-3-ONE AND ALKYLENEBISTHIOCYANATE

[75] Inventors: Osamu Umekawa, Kaizuka; Sakae Katayama, Kobe, both of Japan

[73] Assignees: Katayama Chemical Works Co., Ltd.; Yoshitomi Pharmaceutical Industries, Ltd., both of Osaka, Japan

[21] Appl. No.: 327,011

[22] Filed: Dec. 3, 1981

[30] Foreign Application Priority Data

Dec. 13, 1980 [JP] Japan ................................ 55-176095

[51] Int. Cl.³ ...................... A61K 31/385; D21D 3/00
[52] U.S. Cl. .................................... 514/516; 162/161; 210/764
[58] Field of Search ........................ 424/277; 162/161; 210/764

[56] References Cited

U.S. PATENT DOCUMENTS 4,289,581 9/1981 Katayama et al. ................... 424/277
4,334,957 6/1982 Katayama et al. ................... 424/277

FOREIGN PATENT DOCUMENTS 52-14294 4/1977 Japan .

OTHER PUBLICATIONS

English Trahnslation of Reference L (13 pages).

Primary Examiner—Allen J. Robinson
Attorney, Agent, or Firm—Hubbell, Cohen, Stiefel & Gross

[57] ABSTRACT

This invention relates to microbicidal/microbistatic compositions for industrial use which comprise 4,5-dichloro-1,2-dithiol-3-one and an alkylenebisthiocyanate and a method of killing and/or inhibiting the growth of microbes by using the aforementioned compositions.

12 Claims, 1 Drawing Figure

MICROBICIDAL/MICROBISTATIC COMPOSITIONS AND USE THEREOF EMPLOYING MIXTURES OF 4,5-DICHLORO-1,2-DITHIOL-3-ONE AND ALKYLENEBISTHIOCYANATE

BACKGROUND OF THE INVENTION

1. Field of the Invention

This invention relates to microbicidal/microbistatic compositions for industrial use which comprise 4,5-dichloro-1,2-dithiol-3-one and an alkylenebisthiocyanate; and a method of killing and/or inhibiting microbes by using the aforementioned compositions.

2. Description of the Prior Art 4,5-dichloro-1,2-dithiol-3-one and alkylenebisthiocyanates are known.

The former compound, 4,5-dichloro-1,2-dithiol-3-one, is known to have strong microbicidal/microbistatic activity, especially against Gram negative bacteria (cf. Japanese Patent Publication No. 14294/1977), while alkylenebisthiocyanates are known to have antimicrobidal activity [cf. e.g. CA 51, 13002$^{bc}$ (1959)]. However, both of the aforementioned compounds are insufficient in microbicidal/microbistatic activity against certain Micrococcus strains (e.g. Micrococcus luteus, Micrococcus lysodeikticus).

Microbicidal/microbistatic compositions comprising 4,5-dichloro-1,2-dithiol-3-one and a haloacetic acid ester are proposed by the inventors of this invention (cf. British Patent Publication No. 2052989).

This invention has been completed on the basis of a discovery of the fact that when the abovementioned two types of active ingredients are used in various industrial targets required for microbicidal/microbistatic treatment (especially in papermaking process water), they produce a synergistically potentiated microbicidal/microbistatic activity, retaining their respective microbicidal spectra, and further exert a potent microbicidal/microbistatic activity against Micrococcus strains.

SUMMARY OF THE INVENTION

Accordingly, it is an object of this invention to provide a microbicidal/microbistatic composition comprising 4,5-dichloro-1,2-dithiol-3-one and an alkylenebisthiocyanate. According to another aspect of the invention, there is provided a method of killing or inhibiting the growth of microbes using the above composition.

The compositions and method described herein are particularly useful for controlling slime in process water of papermaking and industrial cooling water, and further for the microbicidal/microbistatic treatment of various industrial materials such as heavy oil sludges, cutting oils, textile oils and so forth.

DESCRIPTION OF THE PREFERRED EMBODIMENT

Figure 1:
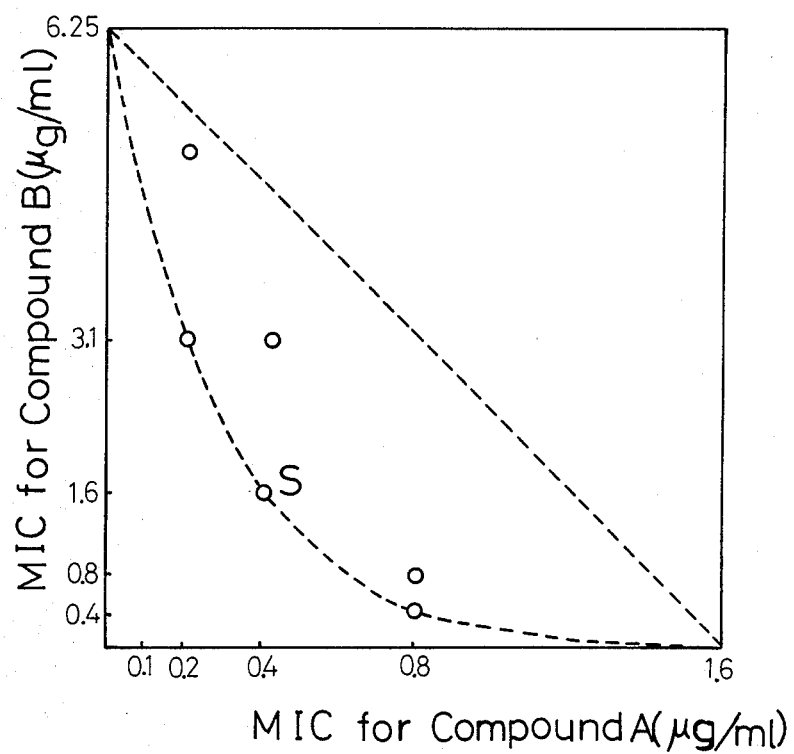
FIG. 1 graphically shows minimum inhibitory concentrations (μg/ml) against Micrococcus luteus as found by the two-dimensional dilution method, the abscissa being for 4,5-dichloro-1,2-dithiol-3-one and the ordinate being for methylenebisthiocyanate.

The alkylenebisthiocyanate to be employed includes methylenebisthiocyanate and ethylenebisthiocyanate, methylenebisthiocyanate being preferred.

The active ingredients are preferably used in the form of a liquid preparation, without limitation thereto. Depending upon the kind of the target materials to be treated, they may be used in the form of a powder preparation.

The solvents to be used in the liquid preparation are suitably organic solvents except water, preferably substantially water-free organic solvents, because 4,5-dichloro-1,2-dithiol-3-one tends to hydrolyze in the presence of water.

The organic solvents for the composition are preferably hydrophilic ones which can dissolve the active ingredients, are miscible with water, can give storable, stable compositions when used with an appropriate surfactant, and can promote dispersion of the active ingredients in water when the composition is added to water systems. Examples of such organic solvents are amides such as dimethylformamide and diethylformamide; glycols such as ethylene glycol, propylene glycol, diethylene glycol and dipropylene glycol; glycol ethers such as methyl cellosolve, ethyl cellosolve, phenyl cellosolve, diethyleneglycol monomethyl ether, propylene glycol monomethyl ether, dipropylene glycol monomethyl ether and tripropylene glycol monomethyl ether; and alcohols having one to eight carbon atoms. Mixtures of two or more of them also may be used. Preferred examples are diethylene glycol, dipropylene glycol, diethylene glycol monomethyl ether dipropylene glycol monoethyl ether and dimethylformamide. The most preferred example is diethylene glycol monomethyl ether.

When the composition is used for microbicidal/microbistatic purposes in various water systems such as papermakingg process water or industrial cooling water, it is preferable to employ a liquid preparation which uses the forementioned hydrophilic organic solvent and a dispersing agent, in consideration of solubility and dispersibility in water of the two active ingredients. Suitable dispersing agents include cationic, anionic, nonionic or amphoteric surfactants. Preferable dispersing agents are nonionic surfactants. The nonionic surfactants include higher alcohol-ethylene oxide (EO) adducts, alkylphenol-EO adducts, fatty acid-EO adducts, fatty acid polyhydric alcohol ester-EO adducts, alkylamine-EO adducts, fatty amide-EO adducts, fat-EO adducts, propylene oxide (PO)-EO copolymers, alkylamine PO-EO polymer adducts, fatty acid glycerin esters, fatty acid pentaerythrytol esters, fatty acid sugar esters, polyhydric alcohol alkyl esters, and alkylolamides.

Preferable are higher alcohol-EO adducts, alkylphenol-EO adducts, fatty acid polyhydric alcohol ester-EO adducts, fatty amide-EO adducts, PO-EO copolymers, polyhydric alcohol alkyl ethers, alkylamine PO-EO copolymer adducts, alkylolamides, and mixtures of two or more of these.

More preferable are such nonionic surfactants as alkylamine PO-EO copolymer adducts (e.g. N,N,N',N'-polyoxyethylene-polyoxypropylene-ethylenediamine) and alkylolamides, Said "N,N,N',N'-polyoxyethylene-polyoxypropylene-ethylenediamines" can be identified as adducts of ethylenediamine and ethylene oxide-propylene oxide block copolymers, and may be prepared by reacting ethylenediamine with propylene oxide and reacting the resultant intermediate adduct with ethylene oxide in accordance with the conventional method. Such surfactants may be represented by the following formula:

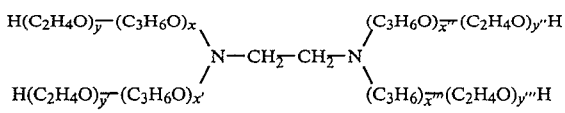

Tetronics ® (Wyandotte Chemical Corp., United States) and Tetronic ® (Asahi Denka Kogyo K.K., Japan) are commercially available products belonging to said class of surfactant.

In practicing the invention, there can be used a wide variety of N,N,N',N'-polyoxyethylene-polyoxypropylene-ethylenediamines having variously different molecular weights, HLB (hydrophilic lipophilic balance) values, forms and other characteristics depending on the amounts specified as desired of ethylene oxide and propylene oxide added respectively and on the manner of combination of these. Generally, however, those wherein the total molecular weight of the propylene oxide units is about 2,000–27,000 and the ethylene oxide unit content is 10–80 percent by weight based on the whole molecule are used.

"Alkylolamide nonionic surfactants" means fatty acid alkylolamides synthesized from fatty acids and alkylolamines. Preferred are the alkylolamides obtained by reaction of higher fatty acids having 8–18 carbon atoms and ethanolamine or diethanolamine. Those that are soluble in water are recommendable. Especially preferred fatty acid alkylolamides are those obtained by reaction of one mole of coconut oil fatty acid (a mixture of higher fatty acids derived from coconut oil) with one or two moles of diethanolamine. As commercially available products there are mentioned Concensate P.A ® (Continental Chemical Co., U.S.A.), Statoamf ® (Nippon Oil & Fats Co., Ltd., Japan) and Profan ® (Sanyo Chemical Ind. Ltd., Japan).

According to circumstances (e.g. in case of no necessity of very high stability of the composition), cationic, anionic or amphoteric surfactants may be used.

A suitable total quantity of the hydrophylic organic solvent and the dispersing agent is less than 99 perts (by weight) per 100 parts (by weight) of the preparation. The preparation usually contains 1–50 parts of 4,5-dichloro-1,2-dithiol-3-one and an alkylenebisthiocyanate, at least 0.01 part of the dispersing agent per part of said two active ingredients, the balance being the hydrophilic organic solvent. The quantity of the dispersing agent is preferably in the range of 0.05–1.0 parts per part of the active ingredients.

The liquid preparation may be prepared in accordance with a conventional method, e.g., by dissolving the active ingredients in the hydrophilic organic solvent and adding to it the surfactant, while stirring, to give a homogeneous solution. The order of dissolution and mixing may of course be reversed.

When the composition of the invention is used for the microbicidal/microbistatic purpose in oils as heavy oil sludges, cutting oils or oily paints, it is preferably in the form of a liquid preparation using a hydrocarbon solvent such as kerosene, heavy oil or spindle oil and optionally containing an appropriate surfactant.

For use in microbicidal/microbistatic target materials in which the two active ingredients can be directly dissolved or dispersed, the active ingredients may be used as they are, or in the form of powder preparation which are diluted with solid diluents (e.g. kaoline, clay, bentonite or carboxymethylcellulose) and optionally contain various surfactants.

The ratio of 4,5-dichloro-1,2-dithiol-3-one to the alkylenebisthiocyanate which produces a synergistic effect is suitably about 1:0.1–1:25 by weight, preferably about 1:0.3–1:16, more preferably about 1:0.5–1:5.0.

The level of addition of the composition depends upon the target materials. For papermaking process water or industrial cooling water, levels of addition of about 0.05 to 20 ppm will be generally adequate for inhibition of growth of microbes (microbistatic use) and levels of addition of about 0.05 to 50 ppm, preferably about 1.0 to 30 ppm will be adequate for microbicidal use.

According to one aspect of this invention, there is provided a microcidal/microbistatic method for industrial use which comprises adding 4,5-dichloro-1,2-dithiol-3-one and an alkylenebisthiocyanate simultaneously, separately or at some time intervals, to the target materials to achieve a synergistic effect.

In the method according to the invention, the simaltaneous addition of the two active ingredients is conveniently made by using the aforementioned preparations which contain both the ingredients. However, separate preparations respectively containing either one and the other of the two active ingredients may be used as desired in certain cases. In these cases, liquid preparations would usually be convenient.

For example, separate preparations for each of the two active ingredients may be prepared by dissolving any of the active ingredients in an appropriate organic solvent and optionally adding a dispersing agent to the resulting solution. In this case, because 4,5-dichloro-1,2-dithiol-3-one is easy to hydrolyze in the presence of water as stated above, its preparation using an anhydrous one of the hydrophilic organic solvents mentioned above is preferable. On the other hand, the solvents for the alkylenebisthiocyanate are the anhydrous hydrophilic organic solvents as well as water-containing organic solvents. If desirable, it may be used in the form of an aqueous preparation. Nonionic surfactants are appropriate for the alkylenebisthiocyanate, although other surfactants may be used.

In the target materials in which each of the two active ingredients can be directly dissolved or dispersed, the ingredients may be as they are or in the form of powder preparation.

A specific example of the method for using separately the two active ingredients is to add firstly 4,5-dichloro-1,2-dithiol-3-one to a system to be treated and add the alkylenebisthiocyanate to a certain specific part of the same system where the remarkable growth of microbes is recognized and a synergistic effect of the two active ingredients is desired. The level of addition and the ratio of the two active ingredients are as stated above.

The two active ingredients, when homogeneously dissolved or dispersed in the target materials, can be expected to exert a potent synergistic microbicidal/microbistatic effect, retaining their respective antibacterial spectra.

Accordingly, it is possible to save a significant quantity of the ingredients, compared with the single use of any of the two active ingredients.

In addition, there can be achieved remarkable microbicidal/microbistatic effects against certain Micrococcus strains, (e.g. *Micrococcus luteus, Micrococcus lysodeikticus*), against which the activity of each of the two active ingredients is insufficient. Accordingly, the compositions and method of this invention are remarkably effective in the systems troubled by mixed bacteria including Micrococcus species.

This invention is useful especially in providing an agent and method for controlling slime which forms in process water in papermaking processes (e.g. in white water pipes or chest walls) or in cooling water in heat exchanger, drain channel and cooling tower of cycle-cooling system. The agent and method are also usable for microbicidal/microbistatic purposes in liquid target materials as heavily oily sludges, cutting oils, lignin-containing waste liquors, various paints, latexes and textile oils.

The following tests and examples illustrate the invention in more detail.

Test 1

Bactericidal Effect

A bouillon medium was inoculated with each of standard bacteria and incubated at optimal temperature for growth. The culture was diluted 100-fold with sterilized water and 10 ml portions of the dilution were poured into sterilized test tubes. Thereto were added mixtures of 4,5-dichloro-1,2-dithiol-3-one and methylenebisthiocyanate in various proportions to see bactericidal effect. Test results are shown below in Table 1.

The ratio of the active ingredients can be understood from the concentration data expressed in terms of weight percent (%) in dimethylformamide (DMF). The quantity of each test solution in DMF which was required to lower the bacterial count from the initial value to $10^3$/ml or less in shown in the table.

In the test, clear synergistic effects are recognized for compositions Nos. 2–5.

TABLE 1

| | Ratio (w/w % in DMF) | | Microbicidal Concentration (ppm) | | |
|---|---|---|---|---|---|
| No. | 4,5-dichloro-1,2-dithiol-3-one | methylenebisthiocyanate | *Pseudomonas aeruginosa* | *Bacillus subtilis* | *Micrococcus luteus* |
| 1 | 3.5 | 0 | 15–20 | 2.5–5 | 20–30 |
| 2 | 3.1 | 1 | 10–15 | <2.5 | 20–30 |
| 3 | 2.7 | 2 | <10 | <2.5 | 15–20 |
| 4 | 2.3 | 3 | <10 | <2.5 | 15–20 |
| 5 | 1.9 | 4 | 10–15 | <2.5 | 20–30 |
| 6 | 1.5 | 5 | 15–20 | 2.5–5 | 20–30 |
| 7 | 1.1 | 6 | 15–20 | 2.5–5 | 20–30 |
| 8 | 0.7 | 7 | 20–30 | 5–10 | 20–30 |
| 9 | 0.3 | 8 | 30< | 10< | 20–30 |
| 10 | 0 | 9 | 30< | 10< | 20–30 |
| Initial number of bacteria per ml | | | $1.1 \times 10^7$ | $7.0 \times 10^6$ | $1.5 \times 10^7$ |

Test 2

Microbistatic effect (1) Test strain

*Micrococcus luteus* isolated from slime.

(2) Test method 4,5-Dichloro-1,2-dithiol-3-one (hereinafter called Compound A) was used as a 50 μg/ml solution (in DMF and its two-fold dilutions, and methylenebisthiocyanate (Compound B) was used as a 100 μg/ml solution (in DMF) and its two-fold dilutions. Microbistatic synergistic effects were examined by the following method.

Synergistic effects were measured by the "two-dimensional dilution method".

Definite quantities of solutions respectively containing Compound A and Compound B at known concentrations were added to a bouillon medium. The medium was inoculated with a definite quantity of a pre-culture of the test strain and incubated at 37° C. for 8 hours under shaking. Concentrations of the respective ingredients at which no increase in absorption at 660 nm was noted any more are called minimum inhibitory concentrations according to the two-dimensional dilution method (hereinafter abbreviated to TDMIC). FIG. 1 is a graphic representation of TDMICs of Compounds A and B in a coordinate system [with usual but such graduation that the minimum inhibitory concentrations of the respective compounds used alone are expressed by an equal length on the respective axes]. In the figure, the area above the curve (TDMIC curve) shows the growth inhibition area and the area below the curve is the growth area. Coincidence of the diagonal line with a TDMIC curve means mere arithmetic addition of actions; a TDMIC curve positioning over the diagonal line means antagonistic action; and a curve positioning below the diagonal line, expresses synergistic effect.

Test results

As shown in FIG. 1, the TDMIC curve clearly indicates synergistic action against Micrococcus luteus, and the optimal effect of the two ingredients which completely inhibited the growth of bacteria is found at TDMICs of 0.4 μg/ml of Compound A and 1.6 μg/ml of Compound B (Point S). In this case, the minimum inhibitory concentrations of Compound A and Compound B are 1.6 μg/ml and 6.25 μg/ml respectively, but in the combined use of A and B, A is required in about one fourth concentration as compared with the use of A alone and B also in about one fourth concentration as compared with B alone. A strong synergistic effect has thus been demonstrated.

Other concentrations of A and B used together which produced a synergistic effect were as shown in Table 2.

TABLE 2

| Concentration of Compound A (μg/ml) | Concentration of Compound B (μg/ml) |
|---|---|
| 0.2 | 3.1 |
| 0.4 | 1.6 |
| 0.4 | 3.1 |
| 0.8 | 0.4 |
| 0.8 | 0.8 |

EXAMPLE 1

Microbistatic effect against white water in paperboard making process.

(1) Test method 9.5 ml of white water from a vat of paperboard making process was poured into an L-shaped test tube, to which 0.5 ml of a high concentration bouillon medium was added. Then, the composition shown below (Compound A or B) was added to a definite concentration. The test tube was shaken at 37° C. in a water bath. The turbidity of the medium in the test tube was monitored by measuring absorbancy at 660 nm at appropriate time intervals from the initiation of culturing. The time required for the absorbancy to reach 0.2 is called the time for growth initiation.

|  | weight parts |
|---|---|
| [Composition A] | |
| 4,5-dichloro-1,2-dithiol-3-one | 3 |
| methylene-bisthiocyanate | 10 |
| diethyleneglycol monomethyl ether | 81 |
| Newpole 2700 | 2 |
| (alkylamine PO-EO copolymer adducts nonionic surfactant supplied by Sanyo Chemical Ind., Ltd., Japan) | |
| Profan 1218 | 4 |
| (alkylolamide nonionic surfactant supplied by Sanyo Chemical Ind., Ltd.) | |
| [Composition B] | |
| 4,5-dichloro-1,2-dithiol-3-one | 2.5 |
| methylenebisthiocyanate | 10 |
| diethyleneglycol monomethyl ether | 80.5 |
| Newpole 2700 | 2 |
| Profan 1218 | 4 |

(2) Test result

Referring to Table 3, microbiotatic synergistic effects are recognized for the compositions of this invention, since the times for growth initiation for the compositions are longer than that of any of the active ingredients.

In Table 3, the addition quantity is expressed in terms of the quantity of the active ingredient. The comparison compositions were solutions of the active ingredients in diethyleneglycol monomethyl ether containing the same surfactant as in Compositions A and B.

TABLE 3

| Composition | Addition quantity of methylenebis-thiocyanate (ppm) | Addition quantity of 4,5-dichloro-1, 2-dithiol-3-one (ppm) | Time for growth initiation (hr) |
|---|---|---|---|
| Blank | 0 | 0 | 2 |
| Comparison 1 | 1 | 0 | 3 |
|  | 2 | 0 | 6 |
|  | 3 | 0 | 10 |
| Comparison 2 | 0 | 0.5 | 10 |
|  | 0 | 1.0 | 15 |
|  | 0 | 1.5 | 22 |
| Composition A | 1 | 0.3 | 13 |
| Composition B | 2 | 0.5 | 25 |

EXAMPLE 2

Microbicidal effect against slime in cooling water.

A large quantity of grey slime formed on the sprinkler board and hot water pit wall of a convenient-size cooling tower in a certain petrochemical plant, whereby the cooling efficacy was remarkably lowered. Microbiological examination identified the slime as bacterial-type one caused by Zooglea strains, Psuedomonas strains, Flavobacterium strains and Bacillus strains, among others.

A composition composed of 10 parts (by weight) of methylenebisthiocyanate, 88 parts of dimethylformamide and 2 parts of Newpole 2700 was poured into the hot water pit, in the quantity equivalent to 50 ppm, for 50 m³ of the retained water in the cooling system, once per three days. After continued operation of the plant for one month, slime was noted on the sprinkler board.

Subsequently, instead of the aforementioned composition, a composition composed of 10 parts of 4,5-dichloro-1,2-dithiol-3-one, 89 parts of dimethylformamide and 1 part of Newpole 2700 was poured into the hot water pit, in the quantity equivalent to 20 ppm, once per three days. After 20 days of operation, slime was noted and the cooling efficacy was lowered.

Then, a composition composed of 2 parts of 4,5-dichloro-1,2-dithiol-3-one, 10 parts of methylenebisthiocyanate, 26 parts of dimethylformamide, 60 parts of diethylene glycol and 2 parts of Newpole 2700 was poured into the hot water pit, in the 20 ppm-equivalent quantity based on the retained water, once per three days. No adhesion of slime on the sprinkler board, hot water pit and cooling pit was recognized and the cooling efficacy was not lowered even after the lapse of 3 months.

EXAMPLE 3

Microbicidal effect against white water in neutral papermaking.

(1) Test method 100 ml of white water which contained Psuedomonas, Flavobacterium, and Micrococcus strains in a certain neutral papermaking plant was poured into a 300-ml polyethylene bottle and the composition specified below (Composition C, D or E) was added to a concentration specified below in Table 4.

The bottle was shaken for an hour. 0.1 ml of the mixture taken from the bottle was diluted with 1000 ml of sterilized water and 1 ml of the dilution was added to a sterile petri dish, to which a bouillon agar medium was added and homogeneously mixed. The mixture was allowed to solidify and them cultured at 37° C. in an incubator for 48 hrs.

The number of viable bacteria was measured by counting the colonies.

|  | parts by weight |
|---|---|
| [Composition C] | |
| 4,5-dichloro-1,2-dithiol-3-one | 5 |
| methylenebisthiocyanate | 10 |
| dimethylformamide | 50 |
| diethyleneglycol | 33 |
| Newpole 2700 | 2 |
| [Composition D] | |
| 4,5-dichloro-1,2-dithiol-3-one | 3 |
| methylenebisthiocyanate | 9 |
| dimethylformamide | 50 |
| dipropylene glycol monomethyl ether | 36 |
| Newpole 2700 | 2 |
| [Composition E] | |
| 4,5-dichloro-1,2-dithiol-3-one | 3 |
| methylenebisthiocyanate | 10 |
| dimethylformamide | 50 |
| dipropylene glycol | 35 |
| Newpole 2700 | 2 |

(2) Test result

Referring to Table 4, it is noted that the compositions of the invention exerted synergistic effect against bacteria, in comparison with single use of each of the two active ingredients. The comparison compositions were solutions of the respective active ingredients in the dimethylformamide-diethylene glycol.

TABLE 4

| Composition | Addition quantity of methylenebis-thiocyanate (ppm) | Addition quantity of 4,5-dichloro-1, 2-dithiol-3-one (ppm) | Number of viable bacteria (per/ml) |
| --- | --- | --- | --- |
| Blank | 0 | 0 | $1.7 \times 10^7$ |
| Comparison 1 | 1.0 | 0 | $8.3 \times 10^6$ |
|  | 3.0 | 0 | $1.6 \times 10^6$ |
|  | 5.0 | 0 | $1.1 \times 10^6$ |
| Comparison 2 | 0 | 0.5 | $1.0 \times 10^7$ |
|  | 0 | 1.0 | $8.0 \times 10^6$ |
|  | 0 | 3.0 | $4.5 \times 10^6$ |
| Composition C | 1.0 | 0.5 | $3.0 \times 10^5$ |
| Composition D | 3.0 | 1.0 | $< \times 10^4$ |
| Composition E | 5.0 | 1.5 | $< \times 10^4$ |

EXAMPLE 4

A field test was conducted in a neutral papermaking plant, from which the white water of Example 3 was taken.

4,5-Dichloro-1,2-dithiol-3-one was continuously added into the plant for 6 hrs per day so as to keep the concentrations of 5 ppm in water. After one week, grey slime was adhered on the wall of white water pit. When measured for the number of viable bacteria, the white water gave a viable count of $6.5 \times 10^7$/ml during the periods of no addition of the ingredient and of $7.0 \times 10^6$/ml during the periods of addition of the ingredient. After washing the paper machine, the continuous addition of methylenebisthiocyanate for 6 hrs per day was resumed to keep the concentration of 5 ppm. On the fourth day, grey slime was noted on the wall of white water pit. The number of viable bacteria in white water was $2.0 \times 10^7$/ml during the periods of no addition and $8.0 \times 10^6$/ml during the periods of addition of the active ingredient.

The paper machine was again washed, and the simultaneous use of 4,5-dichloro-1,2-dithiol-3-one at 1 ppm and methylenebisthiocyanate at 3 ppm for 6 hrs per day was commenced. Even after 3 weeks of operation, slime adhesion on the wall of white paper pit was hardly noted. The production efficacy was improved. The number of viable bacteria in white water was $2.5 \times 10^7$/ml during the periods of no addition and $5.0 \times 10^4$/ml during the periods of addition of the active ingredients. A remarkable bacteriacidal effect was thus demonstrated.

The addition of both of the active ingredients was effected by using the following formulations.

|  | parts by weight |
| --- | --- |
| Formulation (a) |  |
| 4,5-dichloro-1,2-dithiol-3-one | 10 |
| dimethylformamide | 89 |
| Newpole 2700 | 1 |
| Formulation (b) |  |
| methylenebisthiocyanate | 10 |
| dimethylformamide | 88 |
| Newpole 2700 | 2 |

What we claim is:

1. A bactericidal or bacteriostatic composition for industrial use comprising 4,5-dichloro-1,2-dithiol-3-one and methylenebisthiocyanate wherein the ratio of 4,5-dichloro-1,2-dithiol-3-one to methylenebisthiocyanate is of from about 1:0.3 to 1:16.

2. The composition of claim 1 which is in a liquid form in which a hydrophilic organic solvent and a dispersing agent are used.

3. The composition of claim 2 which comprises 1–50 parts (by weight) of both of 4,5-dichloro-1,2-dithiol-3-one and the methylenebisthiocyanate, and at least 0.01 part of the dispersing agent per part of said two active ingredients, the balance being the hydrophilic organic solvent, said composition being substantially free from water.

4. The composition of claim 2, wherein the hydrophilic organic solvent is selected from the group consisting of an amide, a glycol, a glycol ether, an alcohol, and a mixture thereof.

5. The composition of claim 2, in which the dispersing agent is a cationic, anionic, nonionic or amphoteric surfactant.

6. The composition of claim 2, in which the dispersing agent is a nonionic surfactant.

7. The composition of claim 5 or 6 which the nonionic surfactant is an alkylamine-ethylene oxide-propylene oxide copolymer adduct, an alkylolamide surfactant, or a mixture thereof.

8. The composition of claim 1 for use in treating process water in papermaking or industrial cooling water.

9. The composition of claim 2, wherein the hydrophilic organic solvent is dimethylformamide or diethylformamide.

10. The composition of claim 2, wherein the hydrophilic organic solvent is ethylene glycol, propylene glycol, diethylene glycol or dipropylene glycol.

11. The composition of claim 2, wherein the hydrophilic organic solvent is methyl cellosolve, phenyl cellosolve, diethylene glycol monomethyl ether, propylene glycol monomethyl ether, dipropylene glycol monomethyl ether or tripropylene glycol monomethyl ether.

12. The composition of claim 2, wherein the hyrophilic organic sovlent is an alcohol having 1 to 8 carbon atoms.

* * * * *

UNITED STATES PATENT AND TRADEMARK OFFICE
CERTIFICATE OF CORRECTION

PATENT NO. : 4,518,610
DATED : May 21, 1985
INVENTOR(S) : Umekawa et al.

It is certified that error appears in the above—identified patent and that said Letters Patent is hereby corrected as shown below:

At column 1, lined 25, change "$13002^{bc}$" to --$13302^{bc}$--;

At column 2, line 40, change "papermakingg" to --papermaking--.

Signed and Sealed this

Fourth Day of March 1986

[SEAL]

Attest:

DONALD J. QUIGG

Attesting Officer

Commissioner of Patents and Trademarks